United States Patent [19]

Wright et al.

[11] Patent Number: 4,922,893

[45] Date of Patent: May 8, 1990

[54] METHOD FOR PROMOTING FLOW OF A BODY FLUID WITHIN A HUMAN LIMB

[75] Inventors: Edward S. Wright, Pittsburgh; Sonja J. Wright, Sewickley, both of Pa.

[73] Assignee: Wright Linear Pump, Inc., Imperial, Pa.

[21] Appl. No.: 193,539

[22] Filed: May 13, 1988

Related U.S. Application Data

[62] Division of Ser. No. 64,563, Jun. 22, 1987, Pat. No. 4,773,397.

[51] Int. Cl.[5] .......... A61F 5/00

[52] U.S. Cl. .......... 128/64; 128/24 R

[58] Field of Search .......... 128/24 R, 40, 38, 64

[56] References Cited

U.S. PATENT DOCUMENTS

| | | | |
|---|---|---|---|
| 2,531,074 | 11/1950 | Miller | 128/38 |
| 3,920,006 | 11/1975 | Lapidus | 128/40 |
| 4,029,087 | 6/1977 | Dye et al. | 128/24 R |
| 4,030,488 | 6/1977 | Hasty | 128/24 R |
| 4,320,746 | 3/1982 | Arkans et al. | 128/24 R |
| 4,370,975 | 2/1983 | Wright | 128/64 |
| 4,374,518 | 2/1983 | Villanueva | 128/64 |
| 4,702,232 | 10/1987 | Gardner et al. | 128/64 |
| 4,773,397 | 9/1988 | Wright et al. | 128/24 R |
| 4,805,601 | 2/1989 | Eischen | 128/64 |

*Primary Examiner*—Edgar S. Burr
*Assistant Examiner*—Huong Q. Pham
*Attorney, Agent, or Firm*—Carothers & Carothers

[57] ABSTRACT

An improved method and apparatus for promoting flow of a body fluid within a human limb, which has been subjected to an amputation procedure, wherein a novel distal inflatable cell having a pair of inflatable cell portions, one of which encompasses such a limb adjacent the stump end thereof and the other of which extends transversely across the stump end thereof, is utilized in a novel method of therapy to treat Lymphedema and similar fluid accumulation disorders of the extremities.

5 Claims, 1 Drawing Sheet

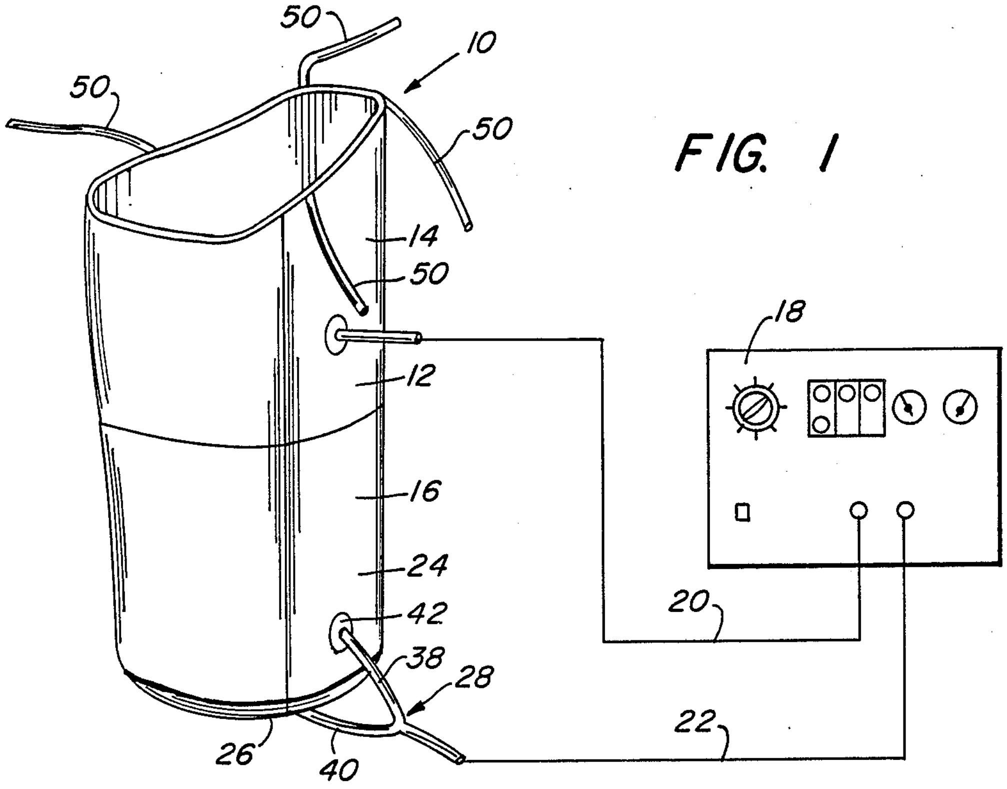
FIG. 1
FIG. 2
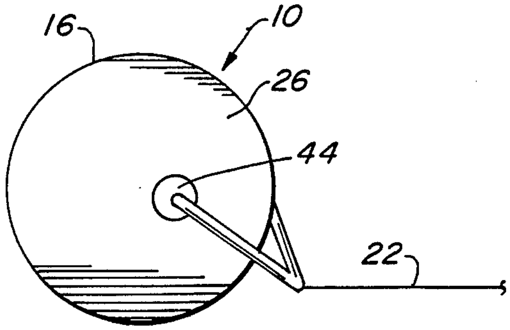
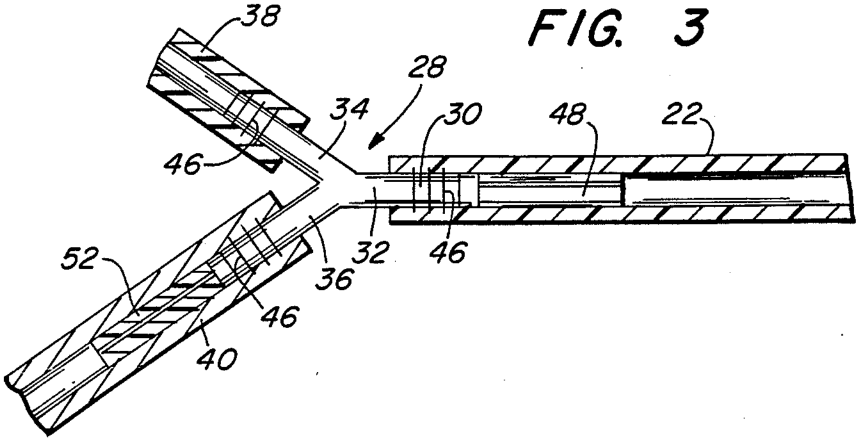
FIG. 3

METHOD FOR PROMOTING FLOW OF A BODY FLUID WITHIN A HUMAN LIMB

This is a divisional of co-pending application Ser. No. 064/563 filed on June 22, 1987, now U.S. Pat. No. 4,773,397.

BACKGROUND OF THE INVENTION

It is well known in the medical arts that the treatment of certain physical conditions benefits markedly by the application of pressure to a body extremity such as an arm or a leg in a manner to promote the flow of a body fluid within the same from a distal portion thereof toward a proximal portion thereof. For example, the afflication known as lymphedema often may cause a limb of the afflicted to swell to a size much greater than normal size as lymphatic fluid accumulates in the limb. One prior mode of treatment for this afflication has been a double-walled sheath or stocking in which air pressure is introduced between the walls to squeeze the limb. It has been found that this and other similar systems which rely on uniform pressure application throughout the length of the afflicated limb do not perform very well and in fact may interfere with the desired distal-to-proximal flow of lymphatic fluid.

Other approaches to treatment of such disorders have included employment of a sheath that is separated into a number of longitudinally spaced inflatable air cells encircling the limb to be treated. These cells are inflated with uniform air pressure successively from the distal end to the proximal end of the sheath with the intent of promoting fluid flow in the desired direction. However, many of these systems also have been ineffectual as they rely on the air pressure being maintained at the same level or magnitude in all of the pressurized cells. U.S. Pat. Nos. 2,533,504 and 2,781,041 disclose examples of such systems.

Prior U.S. Pat. No. 4,370,975 of one of the joint inventors herein discloses an apparatus for treating lymphedema and similar fluid retention afflications through the use of a multi-cell inflatable sheath which encompasses the swollen limb. Pressure is applied in the cells of the sheath in timed sequence from the distal cell to the proximal cell, the sequence of pressure applied also defining a decreasing gradient pressure from a maximum pressure applied in the distal cell to a minimum pressure applied in the proximal cell when all of the cells are pressurized. Generally, for each of the adjacent cells the more distal has applied therein a higher pressure than the more proximal. This application of gradient pressure from distal to proximal cells in time sequence, as described, comprises a cycle, and such cycle may be repeated indefinitely to effectively promote the flow of lymphatic fluid from the afflicted limb in a proximal direction.

Prior to introduction of the advance disclosed by the cited prior U.S. Pat. No. 4,370,975 the art did not contemplate any need or desirability for a cell-to-cell pressure gradient in an inflatable appliance of the sort above described.

BRIEF SUMMARY OF THE INVENTION

We have now invented an improved multi-cell inflatable appliance for use specifically by amputees to achieve the same benefits as are afforded by the appliance disclosed in the above cited U.S. Pat. No. 4,370,975. Specifically, the appliance disclosed in patent 4,370,975 is intended for use primarily on a limb of normal anatomical structure. The disclosed appliance thus contemplates a sheath comprised of multiple inflatable cells arranged side by side to encompass adjacent longitudinal portions of a limb. Because such appliance is well known and fully described in the patent art, further detailed description thereof is believed unnecessary for an understanding of the present invention; however, for purposes of complete disclosure, we hereby incorporate herein, by reference, and make a part hereof the entire disclosure of cited prior U.S. Pat. No. 4,370,975.

The present invention contemplates a novel and improved cell structure for the distal or outermost cell of an inflatable appliance such as above characterized which is improved to provide effective therapeutic benefits for amputees.

In the effort to provide the therapeutic benefits of such an appliance for amputees, several obstacles have been encountered which are overcome by the present invention. For example, an amputee, instead of having a foot or hand at the distal end of the limb to be treated, has only a stump, where the surgical intervention of amputation has been performed. Due to such surgical intervention, the lymph system has been altered and is no longer anatomically complete. The movement of lymphatic fluid under the impetus of pressure applied with an appliance such as disclosed in the incorporated-by-reference patent does not conform to the flow patterns expected and observed in non-amputees. Specifically, there appears to be a tendency in amputees for fluid to move initially toward the distal end or stump end of the limb upon application of pressure in the distal cell of the appliance, whereas no such tendency for proximal-to-distal flow is observed in an anatomically complete limb. Thus, the apparatus of the incorporated-by-reference prior patent, although entirely suitable for most patients, has been found to be significantly less effective in the treatment of amputees. The present invention contemplates the improvement, inter alia, of providing a transverse distal portion of the distal cell which is inflated independently of a separate limb encircling portion of the distal cell in a manner to apply positive pressure to the end of the stump and thereby preclude flow of lymphatic fluid toward the stump end of the limb upon inflation of the distal cell.

In utilizing such improved apparatus for treatment of amputees, the initial application of pressure in the transverse cell portion of the distal cell tends to pull the inflatable sheath down the limb to the point that the transverse portion of the distal cell can no longer exert therapeutically effective pressure on the stump end. The invention therefore also contemplates ties to be utilized to secure the appliance in place on the limb of the amputee and thereby prevent its migration along the limb under the impetus of initially applied pressure on the transverse cell portion. Such ties, however, may introduce undesireable discomfort for the patient. Therefore, it has been further contemplated that the encompassing or encircling portion of the distal cell may initially be inflated sufficiently to create a grip on the portion of the patient's limb adjacent to the stump end to thereby prevent migration of the appliance along the limb under the pressure component applied by the transverse cell portion. This initial inflation of the encircling portion of the distal cell, although very helpful, must be carefully controlled as pressure applied therein which is sufficient to move lymphatic fluid in the limb may, as above noted, tend to move the fluid toward the stump end unless sufficient pressure resisting such flow is applied across the stump end.

As can be seen, the obstacles to effective treatment of amputees present at least one dilemma in that it is desireable to inflate the encircling portion of the distal cell before inflating the transverse portion thereof in order to provide a suitable grip on the limb to prevent sheath migration; however, it is likewise desirable to pressurize the transverse portion of the distal cell before achieving therapeutically effective pressurizion of the encircling portion in order to preclude lymphatic fluid movement toward the stump end of the limb. To overcome these and other obstacles, the invention contemplates the supplying of air under pressure simultaneously through a branched supply line from a single supply source to inflate both the encircling portion and the transverse portion of the distal cell.

It has been found that more gradual inflation of the distal cell than is used for other patients improves the therapeutic benefit for amputees. Accordingly, a flow restriction such as an orifice is provided in the common supply line to reduce the flow rate of pressurized air to both portions of the distal cell. In addition, we have found that one effective way to control the relative rates of inflation and pressurization for the encircling and transverse portions of the distal cell is to provide a second flow restriction orifice in the branch of the supply line which connects to the transverse portion of the cell. The degree of low restriction afforded thereby is determined by considerations of desired therapeutic effect, and the respective volumetric capacities of the encircling and transverse portions of the distal cell. Generally, the transverse portion of the cell has by far the smaller volumetric capacity and therefore would pressurize much more quickly than the encircling portion in the absence of such a flow restriction in the branch supply line connected thereto.

In one preferred embodiment of the invention, a suitable flow restriction is provided by a common extruded plastic wall anchor of the type utilized to set screw fasteners in plaster or dry wall. Such anchors are inserted into the Y branch conduit which connects to the tubing which forms the pressurized air flow supply lines to accord the desired flow restriction therein as above described.

The invention thus affords an improved appliance for use specifically in the treatment of amputees with therapeutic benefit approaching or equalling that available to non-amputees through use of the appliance disclosed in the cited prior U.S. Pat. No. 4,370,975.

It is therefore one object of the invention to provide a novel and improved inflatable appliance for use in the treatment of disorders characterized by disrupted flow and resultant accumulation of body fluids in a limb.

A more specific object of the invention is to provide such an inflatable appliance specifically for use by amputees.

Still another object of the invention is to provide such an appliance wherein a distal cell is comprised of a pair of cell portions, one for encircling a limb and the other for extending across the stump portion of a limb of an amputee, and wherein both the encircling and transverse cell portions are inflatable under the impetus of pressure provided from a single source through a branched conduit system wherein flow restrictions are provided to induce slower than usual inflation of cell portions and a differental inflation and pressurization rate as between the two cell portions, with the cell portions ultimately stabilizing at full inflation under the same magnitude of pressure.

These and other objects and further advantages of the invention will be more clearly understood upon consideration of the following detailed description, and accompanying drawings, in which:

FIG. 1 is a perspective view of an improved inflatable appliance according to one presently preferred embodiment of the instant invention;

FIG. 2 is a bottom plan view of the apparatus of FIG. 1; and

FIG. 3. is a sectional view of a branched air pressure supply line for the apparatus of FIG. 1.

There is generally indicated at 10 in FIGS. 1 and 2 an inflatable sheath apparatus for use in the treatment of lymphedema and similar fluid disorders, the apparatus of FIG. 1 comprising an inflatable, multi-cell sheath 12 provided with a plurality of inflatable cells 14, 16, which are adapted to encompass longitudinally adjacent portions of a human limb to be inflated thereon by means of gradient air pressure supplied in a manner generally consistent with the disclosure of the above cited prior U.S. Pat. No. 4,370,975 through use of a control system 18 and air pressure supply conduits 20, 22. The scheme of operation for apparatus 10 generally contemplates pressurization of the distal cell to a given pressure magnitude with subsequent pressurization of the next adjacent cell 14 to a lower magnitude pressure whereby a pressure gradient from distal to proximal portions of the limb is realized, which pressure gradient is effective to promote lymphatic fluid flow from the limb. Of course it will be understood that the sheath 12 may be comprised of more than two cells, according to the requirements of the specific program of treatment being undertaken.

According to the present invention, cell 16, that is the distal cell of sheath apparatus 12, comprises a limb encircling portion 24 and a transverse portion 26 which extends across the stump end of a limb. The cell portions 24 and 26 are independently inflatable cell portions, each of which is provided with air pressure flow via a branched conduit 28 form a single source of air pressure flow carried within conduit 22. Thus, conduit 22 is connected to a common inlet 30 of a Y connector 32. The branched outlets 34 and 36 of Y connector 32 have respective branch conduits 38 and 40 secured thereon with the opposite ends thereof connected to respective inlet connectors 42 and 44 of respective cell portions 24 and 26.

Conduits 22, 38 and 40 may be, for example, rubber tubing, and Y connector 32 a rigid molded plastic connector with ribbed connector portions as at 46 to be received and retained within the respective ends of conduits 22, 38 and 40. Accordingly, at the beginning of each time cycle of operation in accordance with the disclosure of the prior U.S. Pat. No. 4,370,975 cell 16 is inflated by air pressure flow via conduit 22 connector 32 and conduits 38 and 40 to inflate the encircling and transverse portions 24, 26 of cell 16 for an initial period of pressurization, prior to pressurization of cell 14. As has been noted hereinabove, the relative inflation and pressurization rates of cell portions 24 and 26 must be carefully controlled for reasons cited to ensure effective therapeutic action. Specifically, a first flow regulator in the form of an orifice member 48 is carried within conduit 22 to reduce the rate of inflation and pressurization of cell 16 below that which would otherwise occur in the absence of flow restriction 48. As has been noted, this more gradual inflation of the 16 is believed to result in a more therapeutically beneficial course of treatment for the amputee.

As has been further noted, however, it is also essential that the rates of inflation and pressurization for the respective encircling and transverse portions 24, 26 of cell 16 be regulated to provide optimal therapeutic effect. Because transverse cell portion 26 is of significantly smaller volume than encircling cell portion 24, cell portion 26 will inflate and pressurize much more rapidly under equal flow rates to the two cell portions, and will therefore tend to move the entire sheath 12 downwardly along the limb even if it is secured in place such as by ties 50. Such downward migration of sheath 12 effectively negates therapeutically beneficial pressure application on the end of the stump by transverse cell portion 26. To prevent this, it is necessary that encircling cell portion 24 be sufficiently inflated and pressurized, as transverse cell portion 26 pressurizes, to grip the limb with sufficient force that the position of sheath 12 is maintained, thereby preventing the undesirable downward migration of sheath 12. This initial pressurization of cell portion 24 must not, however, be of such magnitude as to promote any significant flow of lymphatic fluid before therapeutically effective resistance pressure is established in cell portion 26, or else such pressure in cell 24 will promote lymphatic fluid flow toward the stump end of the amputated limb, which is highly undesirable. It has been found that a second orifice or similar flow restricting device 52 of suitable flow control capability may be utilized within conduit 40 to retard inflation and pressurization of cell portion 26 and to thereby establish the desired relationship of inflation and pressurization for the respective cell portions 24 and 26 as above described.

Of course, the specific flow restricting properties of flow regulators 48 and 52 will depend upon numerous factors as above mentioned including, inter alia, the respective volumetric capacities of cell portions 24 and 26, the pressurization and volumetric flow rate capability of control unit 18, and the requirements of the course of treatment specified by the attending physician for the particular condition of his patient.

The effect of flow restriction device 48 thus is to retard the pressurization rates for cell 16 as a whole compared to pressurization rates which have been found to be beneficial for patients who are not amputees. The effect of flow restriction device 52 is to further retard air flow to cell portion 26 with respect to the rate of air flow into cell portion 24. As discussed, this additional retardation of air flow serves to regulate the relative inflation and pressurization rates of cell portions 24 and 26 in accordance with certain desirable modes of operation for the apparatus 10 including, inter alia, maintaining the position of sheath 12 on the limb of the user without undue discomfort, and exerting therapeutically effective pressure on the stump end of the limb and the portion immediately adjacent thereto in a manner to preclude lymphatic fluid flow toward the stump end of the limb.

Flow restriction or regulating devices 48 and 52 may be of any suitable structure, provided that they afford the desired flow regulation capability. We have found that certain sizes of extruded plastic wall anchors of the type commonly utilized to secure threaded fasteners in plaster or dry wall construction serve the purpose quite well, although, of course, the invention is not limited to use of such anchors.

It will also be appeciated that other styles of plastic anchors than those illustrated in FIG. 3 may be utilized. For example, another type of suitable anchor is comprised of an elongated generally tapered member having an enlarged flange or collar adjacent the larger end thereof, which anchor may be inserted within a connector for the rubber tubing, such as in the inlet end 30 of Y-connector 32. Still further, it will be appreciated that flow restrictions devices 48 and 52 need not be located specifically in the positions shown in FIG. 3, so long as they serve to limit or restrict air flow in conduits 22 and 40, as described.

It will be seen from the above description that the present invention also contemplates a novel and improved method of treating lymphedema and similar fluid retention disorders involving abnormal accumulations of body fluids in a human limb. The improved method includes, inter alia, the steps of providing a sheath apparatus having multiple inflatable cells wherein a distal cell includes an encircling portion adapted to encompass a human limb adjacent a stump end thereof, and a transverse portion adapted to extend adjacent such a stump end, providing a first flow of a pressurized medium to inflate the encircling and transverse portions of the distal cell, and inflating and pressurizing the encircling portion of the cell only sufficiently to provide a retention grip on the limb encompassed thereby until the transverse portion of the cell is inflated sufficiently to preclude body fluid flow toward the stump end of the limb when the encircling portion of the cell reaches therapeutically effective pressure to induce body fluid movement. Additional steps of the method may include ultimate equalization of the pressure applied to the human limb by cell portions 24 and 26, and ultimatic pressurization of the adjacent cells of the sheath, in sequence, preferably but not necessarily that a rate of pressurization higher than the maximum rate of pressurization applied to the distal cell and preferably to successively lower magnitudes of pressure to provide a distal-to-proximal pressure gradient.

According to the description hereinabove, there is provided by the instant invention a novel and improved method and apparatus for treatment of lymphedema and similar fluid retention disorders involving abnormal accumulations of body fluid in a human limb, the method and apparatus being especially adapted to be of therapeutic benefit to amputees. Of course, we have contemplated various alternative and modified embodiments of the invention apart from the presently preferred best mode above described, and such would certainly also occur to those familiar with the art, once apprised of our invention. Accordingly, it is our intention that the invention be construed as broadly as permitted by the scope of the claims appended hereto.

We claim:

1. In a treatment for promoting movement of body fluid in a human limb from a relatively distal portion toward a relatively proximal portion thereof by applying thereto pressure components of predetermined magnitudes, the improved method of applying such pressure components comprising the steps of:

initiating application of radially inwardly directed pressure to a given part of said distal portion directly adjacent an outermost end of said distal portion and substantially simultaneously initiating application of longitudinally directed pressure to said outermost end of said distal portion;

simultaneously increasing the magnitudes of said longitudinally directed and radially inwardly directed pressures; and limiting the magnitude of said radially inwardly directed pressure to a magnitude less than the magnitude of said longitudinally directed pressure until said longitudinally directed pressure reaches a first predetermined magnitude which is therapeutically effective for promoting such distal to proximal movement of body fluid.

2. The method as claimed in claim 1 including the additional step of equalizing said radially inwardly directed and said longitudinally directed pressures at said first predetermined magnitude subsequent to said limiting step.

3. The method as claimed in claim 2 including the additional step of further applying radially inwardly directed pressure to at least one portion of such a human limb adjacent said distal portion thereof subsequent to said equalizing step and at a second predetermined magnitude less than said first predetermined magnitude.

4. The method as claimed in claim 3 wherein said further applying step is repeated to apply, in timed sequence, radially directed pressures of decreasing magnitudes to a respective sequence of longitudinally adjacent portions of such a human limb, each of which is relatively proximal with respect to the portion of such a human limb to which pressure is applied in the prior repetition of said further applying step.

5. The method as claimed in claim 4, including the additional step of simultaneously venting all pressures applied to such a human limb subsequent to a final repetition of said further applying step.

* * * * *